US00PP11660P

United States Patent [19]

Meilland

[11] Patent Number: Plant 11,660

[45] Date of Patent: Nov. 28, 2000

[54] HYBRID TEA ROSE PLANT NAMED 'MEIZINCARO'

[75] Inventor: Alain A. Meilland, Antibes, France

[73] Assignee: CP (Delaware), Inc., Wilmington, Del.

[21] Appl. No.: 09/238,743

[22] Filed: Jan. 28, 1999

[51] Int. Cl.[7] ..... A01H 5/00

[52] U.S. Cl. ..... Plt./139

[58] Field of Search ..... Plt./138, 139, 137

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms on an abundant and substantially continuous basis attractive fragrant double blossoms that are Cardinal Red in coloration. The plant exhibits bushy growth habit, glossy foliage, and excellent disease resistance. The new variety is particularly well suited for growing as attractive ornamentation in parks and gardens.

1 Drawing Sheet

SUMMARY OF THE INVENTION

The new variety of Hybrid Tea rose plant (*Rosa hybrida*) was created by artificial pollination wherein two parents were crossed which previously had been studied in the hope that they would contribute the desired characteristics. The female parent (i.e., the seed parent) of the new variety was the product of the cross of the 'Meidaud' variety (non-patented in the United States). and the 'Meisar' variety (non-patented in the United States). The male parent (i.e., the pollen parent) was the 'Meinatac' variety (non-patented in the United States). The 'Meinatac' variety sometimes is known as the 'Susan Hampshire' variety. The parentage of the new variety can be summarized as follows:

('Meidaud'×'Meisar')×'Meinatac'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms on an abundant and substantially continuous basis attractive fragrant double blossoms that are Cardinal Red in coloration, (b) exhibits a bushy growth habit, and (c) is particularly well suited for growing as attractive ornamentation in the landscape.

The disease resistance of the new variety is excellent.

The new variety of the present invention can be readily distinguished from its antecedent cultivars. For instance, the 'Meidaud' variety forms pink blossoms with no fragrance, the 'Meisar' variety forms dark velvety red blossoms, and the 'Meinatac' variety forms pink blossoms and larger leaflets.

The new variety well meets the needs of the horticultural industry and can be grown to advantage in parks and gardens where the brightly colored blossoms contrast nicely with the glossy green foliage.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meizincaro' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing in outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower — plan view — obverse;

FIG. 7—illustrates a specimen of an open flower — plan view — reverse;

FIG. 8—illustrates a specimen of a fully open flower — plan view — bverse;

FIG. 9—illustrates a specimen of a fully open flower — plan view — reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets — plan view— upper surface; and FIG. 15—illustrates a specimen of a leaf with five leaflets — plan view — under surface.

DETAILED DESCRIPTION

Figures 1, 2, 3, 4, 5, 6, 7, 8, 9, 10, 11, 12, 13, 14, 15:
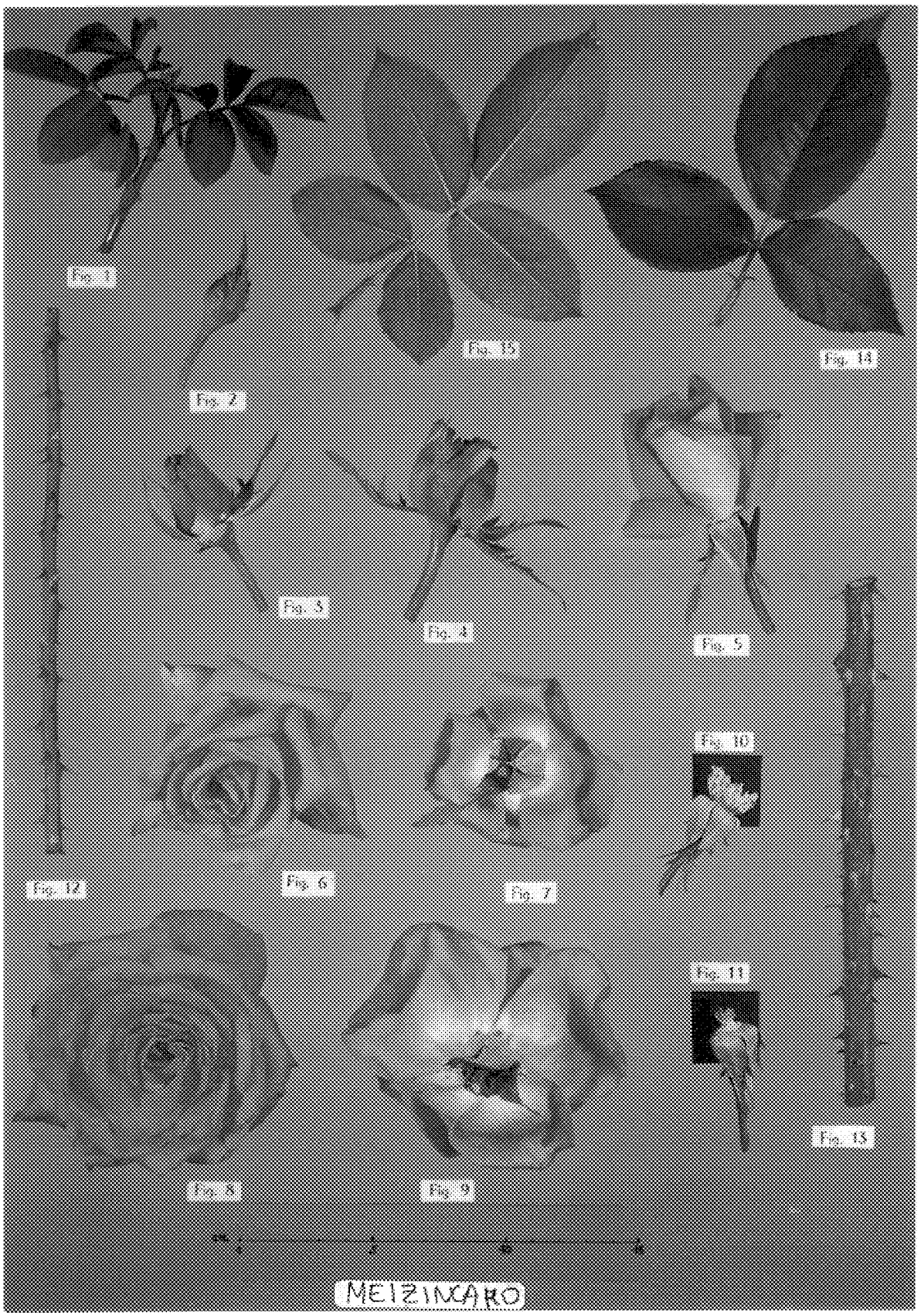

The chart used in the identification of the colors is that of The Royal Horticultural Society (R.H.S. Colour Chart). The description is based on the observation of two year-old plants during June while budded on *Rosa froebelli* understock and growing outdoors at Le Cannet des Maures, Var, France. The coloration in common terms precedes reference to the chart in some instances. Such terminology is to be accorded its ordinary dictionary significance.

Class: Hybrid Tea.

Plant:

*Height.*—Approximately 120 cm. at the end of the second growing season.

*Habit.*—Bushy.

Branches:

*Color.*—Young stems: Light green, Yellow-Green Group 147B. Adult wood: Medium green, Yellow-Green Group 148A.

*Thorns.*—Size: Medium (as illustrated). Quantity: Very numerous (as illustrated). Color: Pinkish on young stems and Havana brown on adult wood.

Leaves:

*Stipules.*—Adnate, pectinate, wide and linear.

*Petioles.*—Upper surface: Striped reddish on young foliage and medium green on adult foliage with glandular edges. Under surface: Light green and bear small prickles and aciculae.

*Leaflets.*—Number: 3, 5 (most often), and 7. Shape: Elliptic. Serration: Single and regular (as illustrated). Texture: consistent. General appearance: Dense and glossy foliage. Color (young foliage): Upper surface: Yellow-Green Group 147A and more or less stained with reddish coloration. Under surface: medium green, Yellow-Green Group 146B and widely stained with reddish coloration. Color (adult foliage): Upper surface: Green Group 139A. Under surface: Greyed-Green Group 191A.

Inflorescence:

*Number of flowers.*—Usually one flower per stem.

*Peduncle.*—Light green, Green Group 143C, more or less stained with reddish coloration, bears small prickles and aciculae, and the length is approximately 5 cm. on average.

*Sepals.*—Upper surface: Tomentose and greenish in coloration. Under surface: Commonly between Green Group 143C and 143D in coloration and commonly with some extensions (as illustrated). Commonly approximately 10 extensions are present per flower, and these commonly average approximately 8 mm in length.

*Buds.*—Shape: Conical. Size: Medium. Length: Approximately 3 cm on average just prior to the parting of the sepals. Width: Approximately 1.5 cm on average just prior to the parting of the sepals. Color upon opening: Upper surface: Near Cardinal Red, Red Group 53A. Under surface: Near Cardinal Red, Red Group 53C.

*Flower.*—Shape: Cupped with parallel sides. Diameter: Approximately 12 cm. on average. Color (when opening begins): Upper surface: Near Spinel Red, Red Group 54A and more or less suffused with Cardinal Red, Red Group 53A. Under surface: Near Cardinal Red, Red Group 53C and more or less suffused with Cardinal Red, Red Group 53A. Color (when blooming): Upper surface: Near Spinel Red, Red Group 54B. Under surface: Near Spinel Red, Red Group 54B with a white area at the base. Color (at end of opening): Upper surface: Near Cardinal Red, Red Group 53D. Under surface: Near Rhodonite Red, Red Group 51C suffused with Cardinal Red, Red Group 53D. Fragrance: Strong, fruity and acidulous. Lasting quality: Very long. The blossoms commonly last approximately 5 days on the plant and approximately 5 days when cut and placed in a vase. Petal number: Commonly approximately 55 on average. Petal shape: Rounded with reflexed edges. Petal drop: Good, the petals commonly detach cleanly. Stamen number: Approximately 125 on average. Anthers: Ochre in coloration. Filaments: Pinkish-yellowish in coloration. Pistils: Approximately 70 on average. Stigmas: Yellowish in coloration. Styles: Pinkish in coloration. Receptacle: Medium green in coloration, smooth, and in longitudinal section in the shape of a pitcher.

Development:

*Vegetation.*—Vigorous.

*Blooming.*—Very abundant and substantially continuous.

*Resistance to diseases.*—Excellent with respect to black spot and powdery mildew.

*Resistance to frost.*—Excellent.

*Fructification.*—Good.

I claim:

1. A new and distinct variety of Hybrid Tea rose plant characterized by the following combination of characteristics:

(a) forms on an abundant and substantially continuous basis attractive fragrant double blossoms that are Cardinal Red in coloration, (c) exhibits a bushy growth habit, and (d) is particularly well suited for growing as attractive ornamentation in the landscape;

substantially as herein shown and described.

* * * * *

MEIZINCARO